United States Patent
Kolahi et al.

(10) Patent No.: US 10,151,728 B2
(45) Date of Patent: Dec. 11, 2018

(54) METHOD FOR OPERATING A RESONANCE-MEASURING SYSTEM AND RESPECTIVE RESONANCE SYSTEM

(71) Applicant: KROHNE Messtechnik GmbH, Duisburg (DE)

(72) Inventors: Kourosh Kolahi, Duisburg (DE); Ralf Storm, Essen (DE); Andreas Poremba, Wuppertal (DE)

(73) Assignee: KROHNE MESSTECHNIK GMBH, Duisburg (DE)

( * ) Notice: Subject to any disclaimer, the term of this patent is extended or adjusted under 35 U.S.C. 154(b) by 36 days.

(21) Appl. No.: 14/419,323

(22) PCT Filed: Jun. 17, 2013

(86) PCT No.: PCT/EP2013/001787
§ 371 (c)(1),
(2) Date: Feb. 3, 2015

(87) PCT Pub. No.: WO2013/189586
PCT Pub. Date: Dec. 27, 2013

(65) Prior Publication Data
US 2015/0219600 A1    Aug. 6, 2015

(30) Foreign Application Priority Data
Jun. 18, 2012   (DE) .................. 10 2012 011 932

(51) Int. Cl.
*G01F 1/84* (2006.01)
*G01N 11/00* (2006.01)
(Continued)

(52) U.S. Cl.
CPC ........... *G01N 27/74* (2013.01); *G01F 1/8422* (2013.01); *G01F 1/8431* (2013.01);
(Continued)

(58) Field of Classification Search
CPC ............... G01N 27/74; G01N 11/10; G01N 2011/0086; G01N 27/00; G01N 3/00;
(Continued)

(56) References Cited

U.S. PATENT DOCUMENTS 4,801,897 A  *  1/1989  Flecken ................ G01F 1/8422
331/155
5,020,380 A      6/1991  Keita
(Continued)

FOREIGN PATENT DOCUMENTS

DE       43 27 052 A1     2/1995
WO       2005/057131 A2   6/2005

OTHER PUBLICATIONS

Joze Kutin, Andrej Smrecnik, Ivan Bajsic, Phase-Locking Control of the Coriolis Meter's Resonance Frequency Based on Virtual Instrumentation, Sensors and Actuators A 104 (2003) pp. 86-93.

*Primary Examiner* — Patrick Assouad
*Assistant Examiner* — Khristopher Yodichkas
(74) *Attorney, Agent, or Firm* — David S. Safran; Roberts Mlotkowski Safran Cole & Calderon, P.C.

(57) ABSTRACT

A method for operating a resonant measurement system has at least one: adjustment device, electric actuation device, electromagnetic vibration generator, vibrating element, and vibration recorder. The adjustment device generates an output signal to trigger the electric actuation device, the electric actuation device provides an electric excitation signal to the electromagnetic drive, the electromagnetic drive excites the vibrating element to the same vibration in at least one normal mode, and the excited vibration is sensed by the vibration recorder and is output as an output signal. To approach, maintain and readjust a resonant point as an operating point of the resonant measurement system, the phase difference between the output signal of the vibration recorder and the adjustment device output signal is acquired, (Continued)

an adjustment deviation is calculated from a predefined phase difference and the acquired phase difference, and the adjustment deviation provided to the adjustment device as an input signal.

11 Claims, 6 Drawing Sheets

(51) Int. Cl.
    *G01N 11/10*     (2006.01)
    *G01N 27/74*     (2006.01)

(52) U.S. Cl.
    CPC .......... *G01F 1/8436* (2013.01); *G01F 1/8468* (2013.01); *G01N 11/10* (2013.01); *G01N 2011/0086* (2013.01)

(58) Field of Classification Search
    CPC ..... G01N 25/00; G01F 1/8468; G01F 1/8436; G01F 1/8431; G01F 1/8422; H05H 1/3405; H05H 1/40; H05H 1/42; H05H 1/341; G01R 33/14; G01R 33/1207
    USPC ........................................................ 324/204
See application file for complete search history.

(56) References Cited

U.S. PATENT DOCUMENTS

| | | | | |
|---|---|---|---|---|
| 5,469,748 | A * | 11/1995 | Kalotay | G01F 1/8413 324/601 |
| 5,497,665 | A * | 3/1996 | Cage | G01F 1/8409 73/861.356 |
| 8,104,361 | B2 | 1/2012 | Kolahi | |
| 8,396,674 | B2 | 3/2013 | Gebhardt et al. | |
| 2003/0212509 | A1* | 11/2003 | Henry | G01F 1/8427 702/45 |

* cited by examiner

METHOD FOR OPERATING A RESONANCE-MEASURING SYSTEM AND RESPECTIVE RESONANCE SYSTEM

BACKGROUND OF THE INVENTION

Field of the Invention

The invention relates to a method for operating a resonance-measuring system, in particular a Coriolis mass flowmeter, wherein the resonance-measuring system includes at least one controller, at least one electric setting device, at least one oscillation element and at least one oscillation sensor, wherein the controller generates a controller output signal $u_1$ for controlling the electric setting device, the electric setting device provides an electric excitation signal for exciting the electromagnetic drive, the electromagnetic drive excites the oscillation element into oscillation in at least one natural mode and wherein the excited oscillation of the oscillation element is detected by the oscillation sensor and is output as at least one output signal. Furthermore, the invention also relates to a resonance-measuring system with which the above-mentioned method can be carried out.

Description of Related Art

Resonance-measuring systems of the above-mentioned type have been known for many years, not only in the form of Coriolis mass flowmeters, but also as density-measuring devices or fill level monitors using the tuning-fork principle, as quartz scales and band viscometers, etc. These resonance-measuring systems are related to a process, wherein process and resonance-measuring system interact.

In the following, resonance-measuring systems are described using the example of Coriolis mass flowmeters, which is to be understood as not be limiting of the invention. In the present, resonance-measuring systems are identified in general as such systems in which information concerning the process variables to be determined (measuring variables) are encoded in the natural modes and/or such systems in which the working point is set at the natural mode of the measuring system. The following designs are applicable to all systems falling under this definition. In Coriolis mass flowmeters, the measuring tube corresponds to the oscillation element of the resonance-measuring system; this particular design of the oscillation element also does not present a limitation for the general teaching being applicable for resonance-measuring systems.

Resonance-measuring systems in the form of Coriolis mass flowmeters are used in industrial process-measuring technology primarily where mass flow needs to be measured with a high accuracy. The functionality of Coriolis mass flowmeters is based on at least one measuring tube—the oscillating element—with medium flowing through it being excited to oscillation by an oscillation generator, wherein this oscillation generator is designed on the premise of being an electromagnetic drive. In such an electromagnetic drive, a coil normally has electric current flowing through it, wherein a force acting on the oscillation element is directly associated with the coil current. In Coriolis mass flowmeters, the functionality is based on the massive medium retroactively affecting the walls of the measuring tube due to the Coriolis force caused by two orthogonal movements—that of the flow and that of the measuring tube. This retroaction of the medium on the measuring tube leads to a change in the measuring tube oscillation compared to the oscillation state of the measuring tube without flow. By detecting these characteristics of the oscillation of the Coriolis measuring tube with flow, the mass flow through the measuring tube can be determined with high accuracy.

The natural modes of the Coriolis mass flowmeter or the oscillateable parts of the Coriolis mass flowmeter are of particular importance, essentially the natural modes of the measuring tube as oscillation element, because the working point of the Coriolis mass flowmeter is normally set at the natural mode of the measuring tube in order to be able to impress the necessary oscillations for the induction of the Coriolis force with a minimum energy input. The oscillations then carried out by the measuring tube have a certain form, which is called the natural mode of the respective excitation.

It is known from the prior art for the controller to generate a harmonic base signal as controller output signal in the form of a sinusoidal voltage for exciting the oscillation element and this sinusoidal voltage activates the electric setting device, wherein the electric setting device has the task of providing a corresponding power at its outlet in order to be able to activate the electromagnetic drive in a suitable manner and with sufficient power. Thus, the electric setting device is, in practice, the performance link between the controller and the electromagnetic drive of the resonance-measuring system.

The controller serves the purpose of operating the oscillation element in resonance, whereto it must be determined whether input and output values of the resonance system have a phase difference corresponding to the resonance. In the case of Coriolis mass flowmeters, on the input side, this is the force with which the measuring tube is excited as oscillation element and, on the output side, this is the velocity of the measuring tube. Due to the correlations forming the basis of this oscillateable system, a resonance is present when the input-side force and the output-side measuring tube velocity have a phase difference $\Delta\varphi$ of 0°. If this phase requirement is fulfilled, the desired resonance is present. For this reason, the control loop for operating a resonance-measuring system of this sort known from the prior art is a phase-locked loop.

Due to the correlation between the flow through a drive coil of the electromagnetic drive and the effective force as electric setting device or as part of an electric setting device, resonance-measuring systems having an electromagnetic drive often have a voltage-controlled current source, which must have a large bandwidth and should barely cause any additional phase shift in the frequency working range. The phase control is thus normally based on a phase measurement between the measuring tube velocity and the driving voltage of the electric setting device with the assumption that the influence of the setting device and/or the electromagnetic drive itself is negligible on the phase difference. This is problematic in various ways.

The impression of the current in the electromagnetic drive having a coil inevitably leads to voltages at the drive coil that are too high and noisy, since the jumps in the controller output signal—even if these are only caused by the quantization stages of a digital/analog converter—occur as jumps in current through the electromagnetic drive and are "differentiated" there by the drive coil; this holds true, in particular, for setting devices with a high slew rate, i.e., with a high increasing velocity of the current. This is problematic in view of the electromagnetic compatibility and also leads to a decrease of the signal to noise ratio and thus to an increase of the measuring inaccuracy in measuring different process variables—mass flow in the case of Coriolis mass flowmeters—and in determining different parameters of the resonance-measuring system—for example the stiffness of the measuring tube in the case of Coriolis mass flowmeters. For this reason, a quick measurement of the drive current is also not possible, since the relatively small drive current is very noisy, which requires a long averaging time until a sufficiently smooth signal is obtained.

SUMMARY OF THE INVENTION

The object of the present invention is to provide a method for operating a resonance-measuring system, which allows a fast and reliable start-up, retaining and updating of a resonance point as working point of the resonance-measuring system.

The method according to the invention for operating a resonance-measuring system, in which the above derived and described object is achieved, is initially and essentially characterized in that the controller-oscillation-sensor-phase-difference between the output signal of the oscillation sensor and the controller output signal is determined in a control loop, a control deviation e is calculated using a predetermined phase difference and the controller-oscillation-sensor-phase-difference, and the control deviation is provided to the controller as an input signal. By choosing a suitable predetermined phase difference, an otherwise unconsidered phase shift between the input signal and the output signal of the oscillation element is corrected.

The method according to the invention initially deliberately forgoes the problematic determination of a state variable of the electromagnetic drive—like the coil current—and instead works using the well-known controller output signal that is known because it is generated by the controller, which is usually implemented in a micro-processor or micro-controller by a digital control algorithm and a subsequent signal generator and is thus available to the user.

The method according to the invention is fast, since measuring times with comparably large time constants in the range of low-pass filtering and smoothing can be avoided, however, it is then accepted that the control result does not reach the resonance point as exactly as when variables of the resonance-measuring system in direct contact with the resonance point have been recorded by measurement. The possible inaccuracy is thus based on the transmission behavior and thus the phase influence of the transmission members between the controller and the electromagnetic drive remaining unconsidered.

In order to be able to carry out a specific correction and in order to be able to implement a predetermined phase shift between the input signal and the output signal of the oscillation element as quickly as possible, the phase shift, in a preferred further development of the method, of all elements of the control loop except that of the oscillation element are determined depending on frequency and stored in the processing unit (e.g., DSP) instrumentally implementing the method (frequency response). Preferably, first, static corrections are derived from this, which can be technically implemented in different manners. Firstly, for example, by adding additional transmission members in the control loop, which carry out a respective phase correction or by providing respective set values for the phase shift between the output signal $u_1$ of the controller and the output signal y of the oscillation sensor.

The predetermined phase difference is chosen according to the transmission behavior of the resonance-measuring system and the relation of the controller output signal $u_1$ and the output signal y of the oscillation sensor. In the case of the Coriolis mass flowmeter as resonance-measuring system described in the introduction, which uses a voltage-controlled current source as electric setting device, the predetermined phase difference would be set at zero in the first approach, so that the determined controller-oscillation-sensor-phase-difference can be traced directly back to the controller as control deviation.

If it were further known that the electric setting device caused a certain mean phase shift in the working point, the predetermined phase difference $\Delta\varphi_{S1}$ could be set, in a first improvement of the method according to the invention, at exactly this value in order to cause a respective compensation of the phase shift. It turns out that the method according to the invention based on the controller-oscillation-sensor-phase-difference leads to good control results in or near to the resonance working point with deviations that are absolutely tolerable in terms of energy.

In the normal case, the predetermined phase difference is chosen such that the oscillation element is excited to oscillation in at least one natural mode in resonance or near the point of resonance. For the purpose of diagnostics, however, it can also be desirable to choose the phase difference to be completely different, for example for the purpose of selective parameter identification, here e.g., at a value of +/−45°.

In a particularly preferred design of the method according to the invention, it is provided that an additional control-drive-phase-difference is formed, namely the phase difference between a state variable $i_S$ of the electromagnetic drive and the controller output signal, wherein this controller-drive-phase difference is then used as predetermined phase difference. It is possible using this additional measure to receive information about the phase shift of those transmission elements located between the controller and the electromagnetic drive, wherein these elements, presently the electric setting device, were deliberately not taken into consideration for implementing the above-described faster control loop that is intentionally kept less precise.

In a modification of the above-described method, it is provided that, once again, a controller-drive-phase-difference between a state variable $i_S$ of the electromagnetic drive and the controller output signal is determined, wherein the predetermined phase difference $\Delta\varphi_{S1}$ is calculated this time using the controller-drive-phase-difference and a further predetermined phase difference. This measure makes it possible to provide the phase control loop, in turn, a phasing from outside deviating from the "normal" working point, for example for the purpose of diagnostics.

The method according to the invention surprisingly has further advantages. The control of the resonance-measuring system based on the control-oscillation-sensor-phase-difference, in particular with an additional correction using the determination of the controller-drive-phase-difference, works so well that a coordination of the control loop, in particular a coordination of the electric setting device, is not longer necessary at a high bandwidth, so that the electric setting device no longer has to be implemented with fast and comparably expensive components, since the control according to the invention is guaranteed at a sufficient speed for keeping the phase shift in a frequency working range below a predetermined value. In the method known from the prior art, the quality of control is significantly dependent on the phase shift caused by the electric setting device, wherein it should be taken into consideration here, that at greater phase shifts, in particular, direct feedback resonance-measuring systems are inclined to oscillation. Thus, these have to be designed in the prior art so that the phase shift caused by the electric setting device—for example a voltage-controlled current source—remains in a working frequency range, for example, below 5°, which leads to the use of expensive reference components and analog correction circuits. This is not longer required in the method according to the invention having a faster control loop based on the controller-oscillation-sensor-phase-difference and having a slower calculation of the correction value based on the controller-drive-phase-difference.

The object derived above is further met with the resonance-measuring system described in the introduction in that a control loop is designed there in such a manner that the above-mentioned method for operating a resonance-measuring system is specifically executable by the resonance-measuring system and is carried out in standard operation—tuning, holding, and updating of a resonance working point. "Executable" accordingly meaning that the method is implemented in the resonance-measuring system for operation and not that it simply only could be implemented in the resonance-measuring system.

In detail there are numerous possibilities for designing and further developing the method according to the invention and the resonance-measuring system according to the invention. Here, reference is made to the description of preferred embodiments in conjunction with the accompanying drawings.

DETAILED DESCRIPTION OF THE INVENTION

Figure 1:
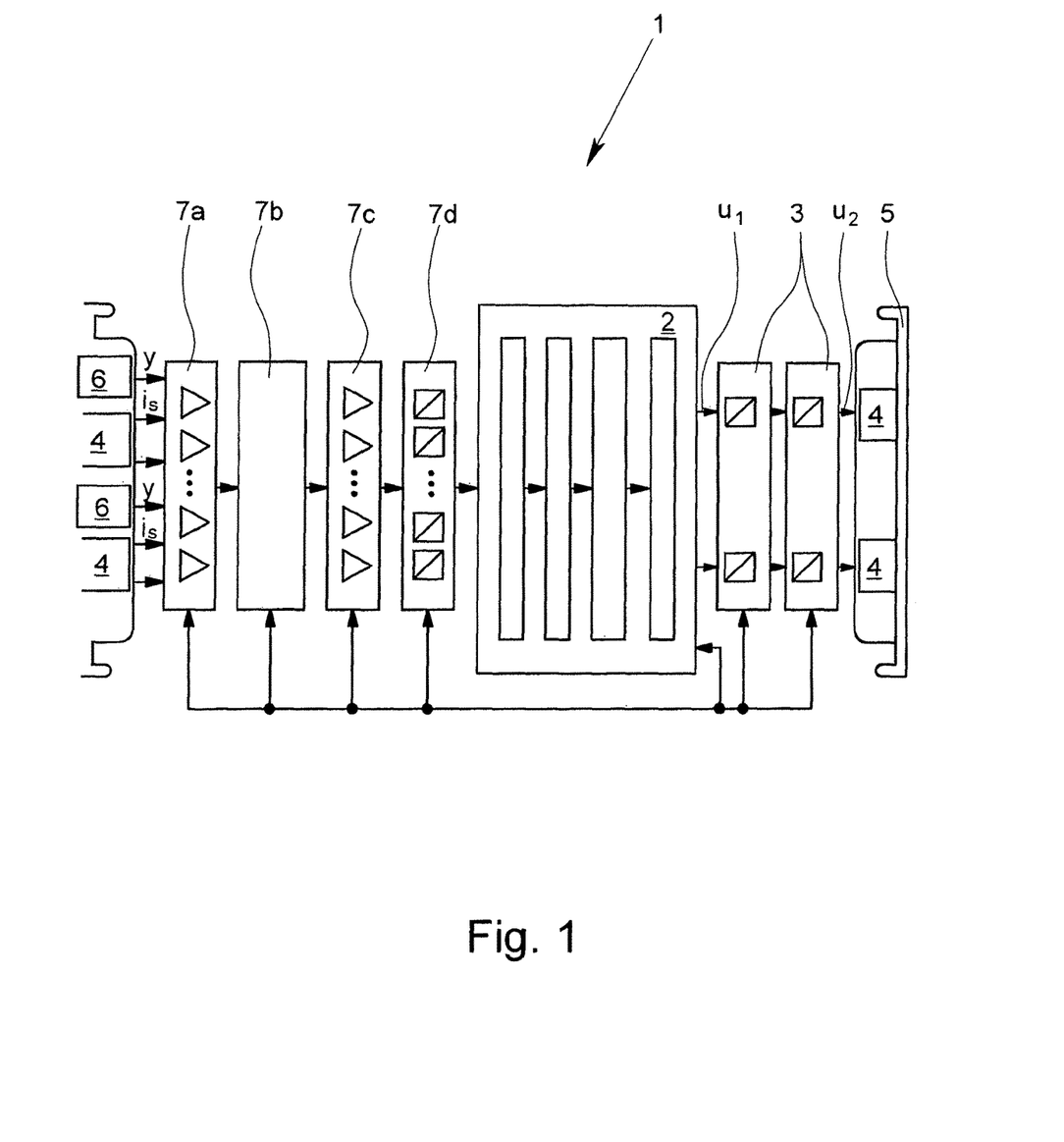
FIG. 1 schematically shows the structure of a resonance-measuring system in the form of a Coriolis mass flowmeter as it is known from the prior art as it could be used for the method according to the invention.

FIG. 1 shows a resonance-measuring system 1 in the form of a Coriolis mass flowmeter, wherein the resonance-measuring system 1 has a controller 2 implemented in a digital signal processor, an electronic setting device 3, and an electromagnetic drive 4 as oscillation generator.

The electromagnetic drive 4 has the function of exciting an oscillation element 5, presently a measuring tube flowable with medium, to oscillation in a natural mode. Depending on the type of natural mode, only one single electromagnetic drive 4 is necessary for this, however, if higher modes are to be excited, two or more electromagnetic drives 4 may be necessary.

In FIG. 1, the resonance-measuring system 1 in the form of a Coriolis mass flowmeter is shown in two parts. The Coriolis mass flowmeter forming one unit ends at one half on the right side of the drawing and begins with the other half on the left side of the drawing for a more clear representation. It can be seen there that the resonance-measuring system 1 also has oscillation sensors 6 that emit an output signal y, presently in the form of a velocity signal, which provides information about the velocity movement in the measuring tube, i.e., the oscillation element 5. The controller 2 generates a controller output signal $u_1$ for controlling the electric setting device 3 and the electric setting device 3 subsequently generates an electric excitation signal $u_2$ for exciting the electromagnetic drive 4. Several transmission elements connect to the oscillation sensor 6, which are essentially used for signal processing, such as, for example, adaptation electronics 7a consisting of amplifiers, a hardware multiplexer 7b for implementing different switchable measuring channels, a further adaptation electronics 7c and an analog/digital converter 7d, which returns the analog measured signals back to the controller 2 in the form of digital signals.

In the prior art, the control loop implemented in this manner forms a phase control loop and is based on the impression of a current is in a coil 8 of the electromagnetic drive 4. This concept is shown again in FIG. 2 for clarification; the electromagnetic drive 4 has a drive coil 8 here, which has a coil inductivity $L_S$, an ohmic coil resistance $R_S$, and an induced voltage source $u_iS$ proportional to the velocity ($u_S = i_S R_S + L * di_S/dt + k * dv/dt$) in the equivalent circuit diagram according to FIG. 2. The electric setting device 3 operates with a voltage-controlled current source 9, which receives quantized voltage signals from a digital/analog converter 10, which leads to erratic changes of the coil current is at the outlet of the voltage-controlled current source 9. This current impression inevitably leads to even more turbulent changes of the terminal voltage us at the coil 8, which also leads to a noisy current signal $i_s$ due to different influences.

Figure 2:
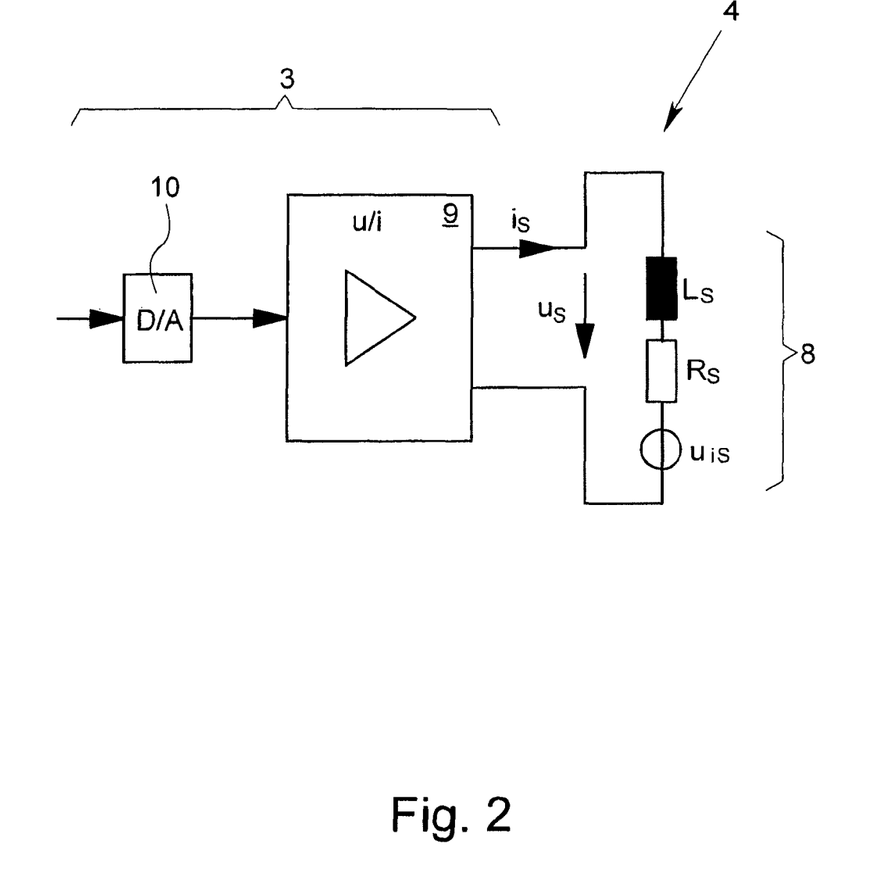
FIG. 2 is an equivalent circuit diagram of a coil contained in an electromagnetic drive with an electric setting device.
Figure 3:
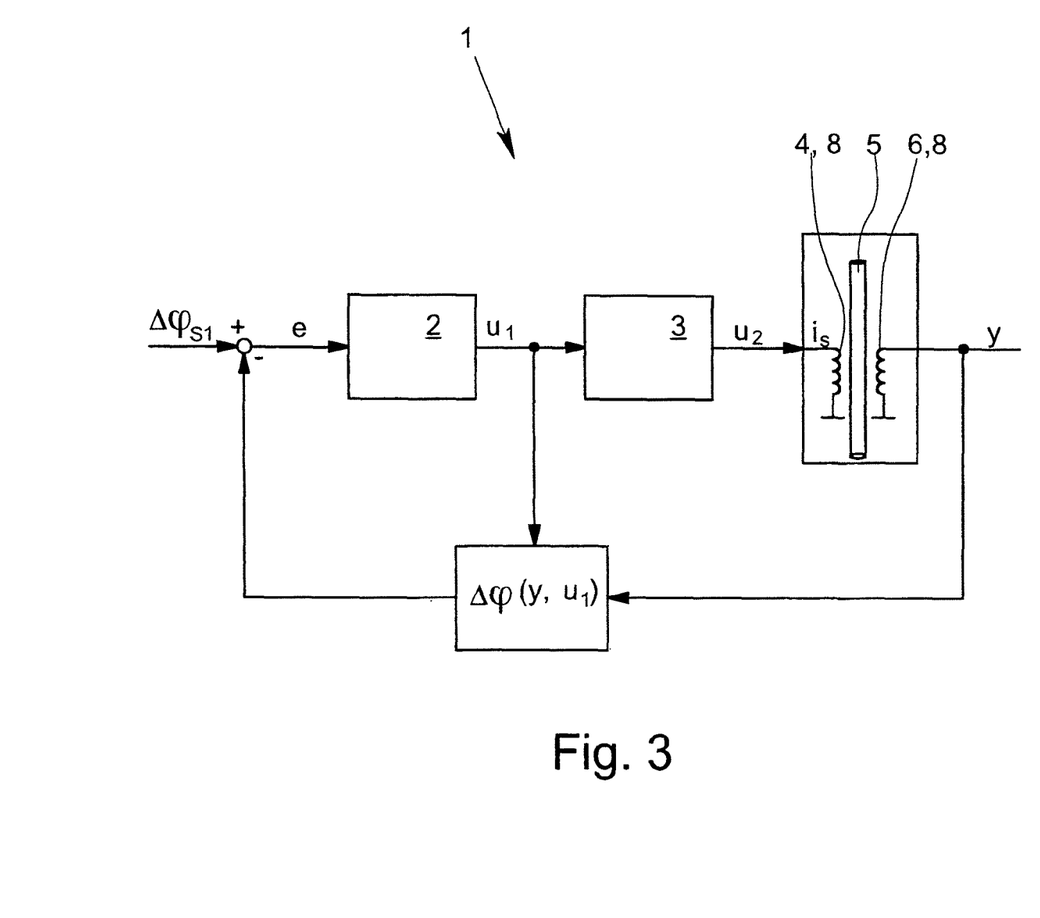
FIG. 3 is a block diagram of the method according to the invention for operating a resonance-measuring system.

In the electromagnetic drive 4, which, as shown in FIG. 2, has a coil 8, the coil current $i_S$ is of particular importance, because the coil current $i_S$ is that state variable of the electromagnetic drive 4 that is proportional to the force of the electromagnetic drive 4 on the oscillation element 5. In the case of a Coriolis mass flowmeter as resonance-measuring system 1, the phase difference between the force acting on the oscillation element 5 and thus also between the coil current $i_S$ and the detected velocity y of the measuring tube movement is zero where resonance occurs. The implementation of a phase control at the resonance working point using the coil current $i_S$ as input variable and state variable of the electromagnetic drive and using the velocity signal as output signal y of the oscillation sensor 6 is problematic: the requirements on the used electric components is, then, very high, since broadband components having low phase deviations in the working point have to be used, which makes this solution expensive overall.

The method for operating a resonance-measuring system 1 according to the invention is shown in FIG. 1, namely is shown in the form of a block diagram. The controller 2 controls the electric setting device 3 via the controller output signal $u_1$, wherein the electric setting device 3 controls the electromagnetic drive 4 using the output of electric excitation signals $u_2$ that deflect the oscillation element 5 as oscillation generator, which is present here as a measuring tube of a Coriolis mass flowmeter. The electromagnetic drive 4 consists of a schematically-illustrated coil 8 with a permanent magnetic as its core, wherein the (not shown) permanent magnet carries out a stroke movement when the coil 8 is fed a current and, in this manner, can excite the oscillation element 5 to oscillation. The oscillation of the oscillation element 5 is detected by the oscillation sensor 6, which, in the present case, also has a permanent magnet and a coil, wherein the voltage induced in the coil 8 is used for evaluating the change of position of the oscillation element 5. The velocity signal is presently the output signal y of the oscillation sensor 6.

The method according to the invention provides that initially the controller-oscillation-sensor-phase-difference $\Delta\varphi(y, u_1)$ is detected between the output signal y of the oscillation sensor 6 and the controller output signal $u_1$ and a control deviation is calculated using a predetermined phase difference $\Delta\varphi_{S1}$ and this controller-oscillation-sensor-phase difference $\Delta\varphi(y, u_1)$, wherein this control deviation e is provided to the controller 2 as an input signal. Thus, a control loop is implemented that controls based on the controller-oscillation-sensor-phase-difference $\Delta\varphi(y, u_1)$ and not based on the phase difference that is actually decisive for a control based on the resonance point of the resonance-measuring system, presently, namely, the phase difference between the coil current $i_S$ and the velocity signal y at the outlet of the oscillation sensor 6. Thus, an error is accepted, namely the unconsidered phase shift, which is caused by the electric setting device 3. This phase shift is incorrectly—but deliberately—added to the core of the resonance-measuring system 1, namely the electromagnetic drive 4, the oscillation element 5 and the oscillation sensor 6. The advantage of the method according to the invention is that a very fast control can be implemented with a working point that is quite close to the resonance point of a resonance-measuring system 1 using the control based on the controller-oscillation-sensor-phase difference $\Delta\varphi(y, u_1)$ with comparably non-noisy signals, so that, with a small limitation in resonance phasing, a downright fast control can be implemented, a control that additionally no longer requires the use of components with a large band width and requires only a very small phase shift of the electric setting device in the working frequency range.

In the simplest case, the predetermined phase difference $\Delta\varphi_{S1}$ is set at the value that would result as phasing or phase difference between the controller output signal $u_1$ and the output signal y of the oscillation sensor 6 if the electric setting device 3 caused practically no phase shift and the resonance case were set. In the case shown of the Coriolis mass flowmeter, this corresponds to setting the predetermined phase difference $\Delta\varphi_{S1}$ to zero; in this form, the oscillation element 5 is excited to oscillation in a natural form in resonance or near the resonance point.

Figure 4:
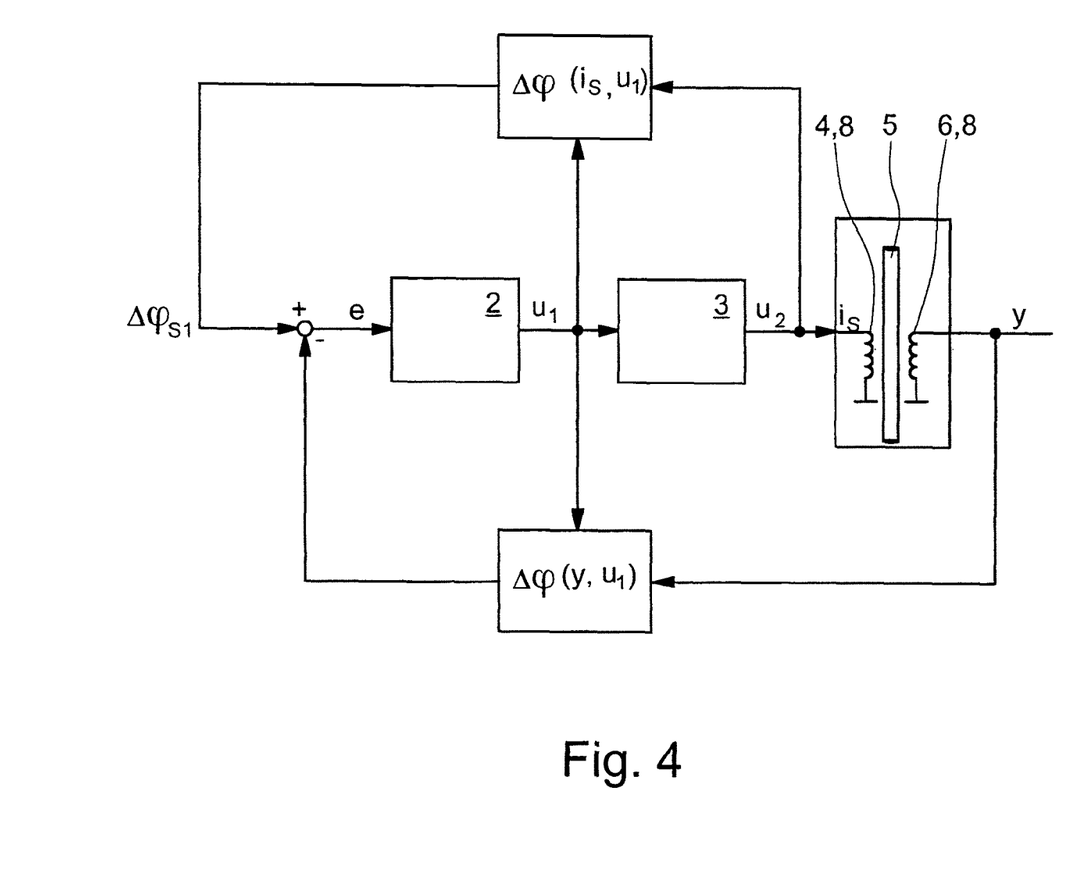
FIG. 4 is a block diagram of a further embodiment of the method according to the invention for operating a resonance-measuring system.

A further embodiment of the above-described method is shown in FIG. 4, in which a controller-drive-phase-difference $\Delta\varphi(i_S, u_1)$ between the state variable $i_S$ of the electromagnetic drive 4 and the controller output signal $u_1$ is determined, wherein the controller-drive-phase-difference $\Delta\varphi(i_S, u_1)$ is then used as predetermined phase difference $\Delta\varphi_{S1}$. The error accepted above in the phase control is compensated again due to this measure.

Figure 5:
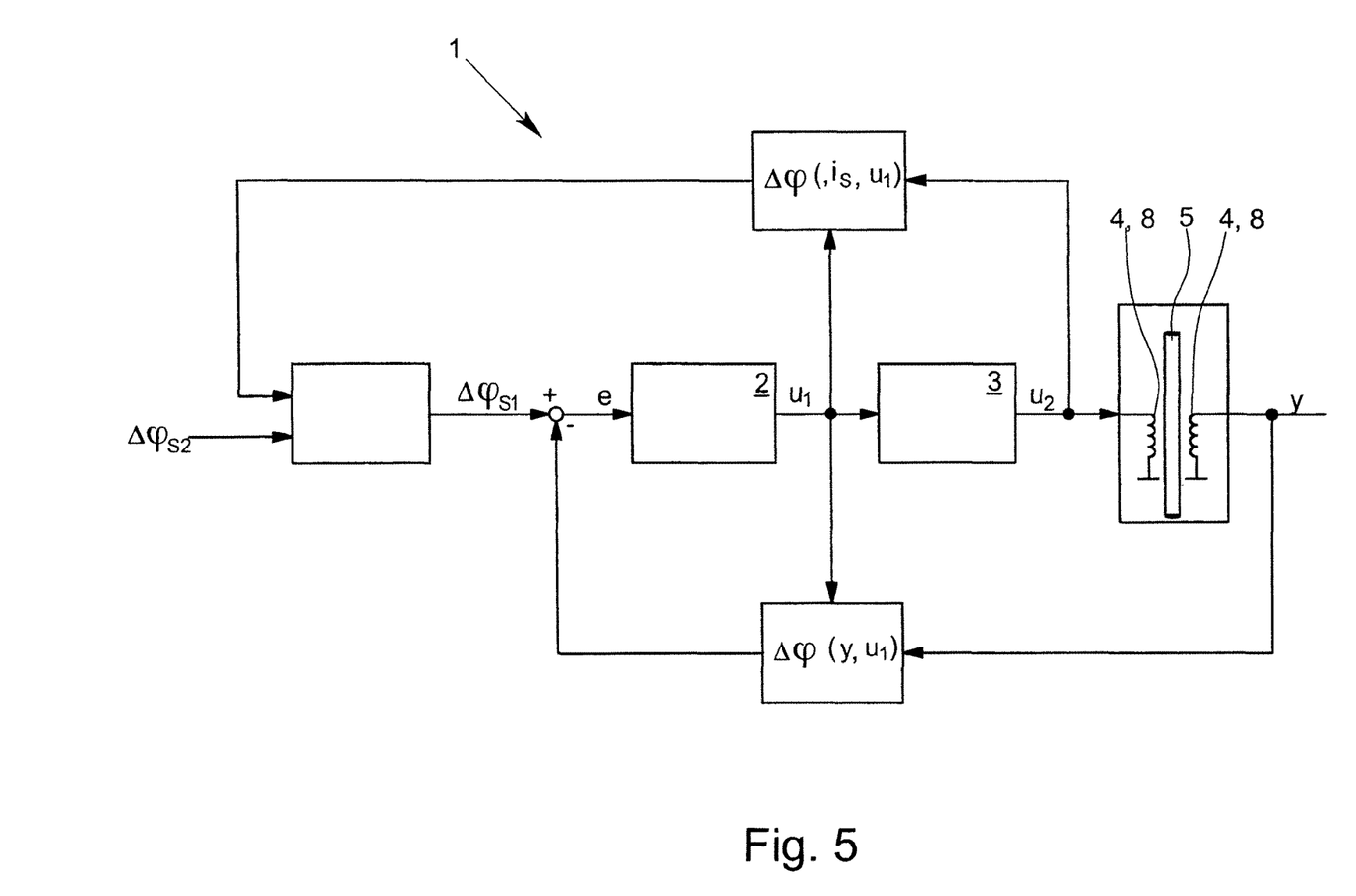
FIG. 5 is a block diagram of another further developed embodiment of the method according to the invention for operating a resonance-measuring system and FIG. 6 is a block diagram of a final further developed embodiment of the method according to the invention for operating a resonance-measuring system with a view of the components.

In the further development of the method shown in FIG. 5, the controller-drive-phase-difference $\Delta\varphi(i_S, u_1)$ is also initially additionally determined between the state variable $i_S$ of the electromagnetic drive 4 and the controller output signal $u_1$, wherein, then, the predetermined phase difference $\Delta\varphi_{S1}$ is calculated using the controller-drive phase difference $\Delta\varphi(i_S, i_1)$ and a further predetermined phase difference $\Delta\varphi_{S1}$, which allows other phase specifications and also other operation modes, for example a phase-selective excitation of the Coriolis mass flowmeter at a phase specification of $\Delta\varphi_{S2}=+/-45°$.

In both variations of the method shown in FIGS. 4 and 5, the current detected in the drive coil 8 employed there is used as state variable $i_S$ of the electromagnetic drive 4.

The method described as yet allows the use of a voltage-controlled current source as electric setting device 3, as well as a voltage-controlled current source that meets only a few high requirements, such as those requirements known from the prior art for phase control that are directed toward the immediate input and output variables of the resonance section. This allows for the use of economical standard components.

Of particular advantage is that the method can be used when the electric setting device 3 provides a voltage $u_S$ as electric excitation signal $u_2$ for exciting the electromagnetic drive 4, which is the case in FIGS. 3 to 6, here the voltage $u_S$ is applied as supply voltage of the drive coil 8 of the electromagnetic drive 4. This also makes sense for the solitary—fast—phase control based on the controller-oscillation-sensor-phase-difference $\Delta\varphi(y, u_1)$ between the output signal y of the oscillation sensor 6 and the controller output signal $u_1$, and makes sense for an additional correction of the predetermined phase difference $\Delta\varphi_{S1}$ by determining the controller-drive-phase-difference $\Delta\varphi(i_S, u_1)$ between the state variable $i_S$ of the electromagnetic drive 4 and the controller output signal $u_1$. In any case, the current impression and the consequent and above-described interference are avoided.

FIG. 6 again shows a resonance-measuring system 1 in greater detail in the form of a Coriolis mass flowmeter, wherein the resonance-measuring system 1 has a controller 2a, 2b implemented in a digital signal processor (DSP), an electric setting device 3 with a digital/analog converter 3a and a voltage-controlled voltage source 3b as power unit. As in the above examples, the electromagnetic drive 4 has a coil 8 as oscillation generator.

Figure 6:
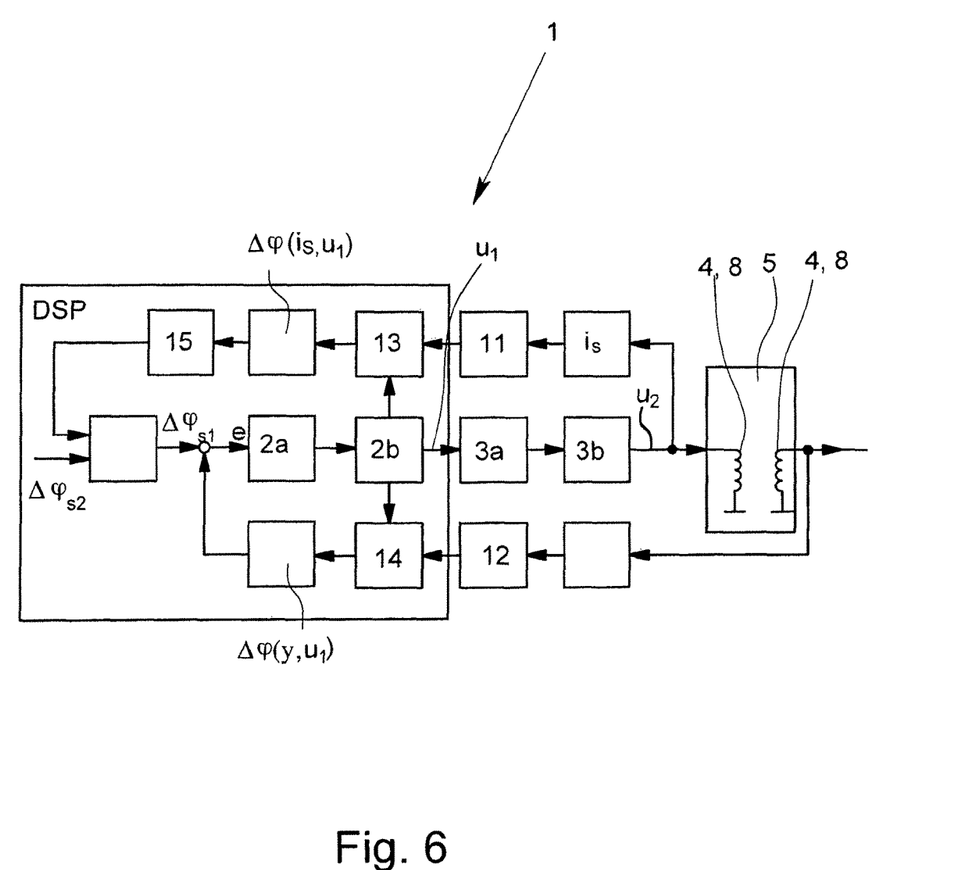

The fast control loop is implemented in the lower signal path, which is based on the controller-oscillation-sensor-phase-difference $\Delta\varphi(y, u_1)$ between the output signal y of the oscillation sensor 6 and the controller output signal $u_1$. The—slower—calculation of the correction value for the phase difference is implemented in the upper signal path, which is based on the controller-drive-phase-difference $\Delta\varphi(i_S, u_1)$ between the state variable $i_S$ of the electromagnetic drive 4 and the controller output signal $u_1$. The detected current signal as well as the detected velocity signal y are digitized by an analog/digital converter 11, 12 and fed to the DSP. Demodulators 13, 14 dismantle the measuring variables $i_S$,y with the help of orthogonal base signals in signal components, which allow for the determination of the phasing of the signals in respect to the base signal $u_1$, wherein the controller-drive-phase-difference $\Delta\varphi(i_S, u_1)$ is also filtered over a low pass filter 15 and wherein this low pass filter has a time constant of about two seconds.

The implementation of the electric setting device 3 as voltage-controlled voltage converters has the further unexpected advantage that the low output resistance of the voltage-controlled voltage converter acts as a "short-circuit" in view of the drive coil 8 and thus a damping of the oscillation of the measuring tube is achieved depending on the velocity of the measuring tube. Thus, the installation of short-circuit loops in the electromagnetic drive 4 for the purpose of damping of the generally weakly damped system can be omitted.

What is claimed is:

1. Method for operating a resonance-measuring system having at least one controller, at least one electric setting device, at least one electromagnetic drive with a drive coil, at least one oscillation element and at least one oscillation sensor, comprising the steps of:
  using said at least one controller to generate a controller output signal $u_1$ for controlling the electric setting device, wherein the at least one electric setting device provides a voltage $u_s$ as an electric excitation signal $u_2$ for exciting the electromagnetic drive, and wherein the voltage $u_2$ is applied as a terminal voltage of the drive coil of the electromagnetic drive, using the electric setting device to provide an electric excitation signal $u_2$ for exciting the electromagnetic drive, using the electromagnetic drive to excite the oscillation element into oscillation in at least one natural mode, detecting the excited oscillation of the oscillation element with the oscillation sensor and outputting the detected excited oscillation as at least one output signal y based on the excited oscillation detected, using an electronic circuit for determining a controller-oscillation-sensor-phase-difference between the output signal of the oscillation sensor and the controller output signal $u_1$ in a control loop on the basis of the output signal and a measured controller output signal, using a digital signal processor for calculating a control deviation e using a predetermined phase difference and the determined controller-oscillation-sensor-phase-difference, separately determining a controller-drive-phase-difference on the basis of the measured controller output signal u_1 and a measured current in the coil of the electromagnetic drive, and using the controller-drive-phase-difference $\Delta\varphi(i_s, u_1)$ as the predetermined phase difference, and providing the control deviation to the controller as an input signal of a control loop for ongoing control of the electric setting device so to adjust excitation of the oscillation element into oscillation close to the resonance point of the resonance-measuring system based on the controller-oscillation-sensor-phase difference.

2. Method according to claim 1, wherein the predetermined phase difference is chosen such that the oscillation element is excited to oscillation in at least one natural mode in resonance or near a point of resonance.

3. Method according to claim 1, wherein the determined controller-drive-phase-difference is filtered with a low-pass filter having a time constant in a seconds range.

4. Method according to claim 3, wherein a harmonic base signal is generated by the controller as the controller output signal $u_1$ for determining at least one of the controller-oscillation-sensor-phase-difference and the controller-drive-phase-difference $\Delta\varphi(i_s, u_1)$, wherein each phase difference is determined using demodulation of each signal y, $i_s$ of interest with the harmonic base signal and a further harmonic base signal, orthogonal to the first harmonic base signal, provided by the controller.

5. Method according to claim 1, wherein one of mass flow rate, density and fill level is determined from an output of the system.

6. Resonance-measuring system, comprising:
an electromagnetic drive,
at least one controller,
at least one electric setting device,
at least one oscillation element, and
at least one oscillation sensor,
wherein the controller is configured for generating a controller output signal for controlling the electric setting device,
wherein the electric setting device is adapted to provide an electric excitation signal for exciting the electromagnetic drive,
wherein the electromagnetic drive is configured for exciting the oscillation element into oscillation in at least one natural mode,
wherein the oscillation sensor is configured for detecting excited oscillation of the oscillation element and for outputting at least one output signal, and
wherein a control loop is formed on the basis of the output signal and the controller output signal in such a manner that a controller-oscillation-sensor-phase-difference between the output signal of the oscillation sensor and the controller output signal determined on the basis of the controller output signal and the current in the coil of the electromagnetic drive and controls the electric setting device so to adjust excitation of the oscillation element into oscillation close to the resonance point of the resonance-measuring system.

7. Resonance-measuring system according to claim 6, wherein the electric setting device is a voltage-controlled voltage transformer.

8. Resonance-measuring system according to claim 6, wherein the system is a Coriolis mass flowmeter.

9. Method for operating a resonance-measuring system having at least one controller, at least one electric setting device, at least one electromagnetic drive with a drive coil, at least one oscillation element and at least one oscillation sensor, comprising the steps of:

using said at least one controller to generate a controller output signal for controlling the electric setting device, using the electric setting device to provide an electric excitation signal for exciting the drive coil of the electromagnetic drive, wherein the electric setting device provides a voltage us as an electric excitation signal for exciting the electromagnetic drive, and wherein the voltage us is applied as a terminal voltage of the drive coil of the electromagnetic drive, using the electromagnetic drive to excite the oscillation element into oscillation in at least one natural mode, detecting the excited oscillation of the oscillation element with the oscillation sensor and outputting the detected excited oscillation as at least one output signal y based on the excited oscillation detected, using an electronic circuit for determining a controller-oscillation-sensor-phase-difference between the output signal of the oscillation sensor and the controller output signal $u_1$ in a control loop on the basis of the output signal and a measured controller output signal, using a digital signal processor for calculating a control deviation e using a predetermined phase difference and the determined controller-oscillation-sensor-phase-difference, determining a controller-drive-phase-difference between a state variable of the electromagnetic drive and the controller output signal on the basis of the measured controller output signal and a measured current in the coil of the electromagnetic drive, and separately calculating the predetermined phase difference $\Delta\varphi_{S1}$ using the determined controller-drive-phase-difference and an additional predetermined phase difference $\Delta\varphi_{S2}$, using the current of the drive coil as the state variable of the electromagnetic drive, providing the control deviation to the controller as an input signal of a control loop for ongoing control of the electric setting device so to adjust excitation of the oscillation element into oscillation close to the resonance point of the resonance-measuring system.

10. Method according to claim 9, wherein the determined controller-drive-phase-difference is filtered with a low-pass filter having a time constant in a seconds range.

11. Method according to claim 9, wherein a harmonic base signal is generated by the controller as the controller output signal for determining at least one of the controller-oscillation-sensor-phase-difference and the controller-drive-phase-difference, wherein each phase difference is determined using demodulation of each signal, is of interest with the harmonic base signal and a further harmonic base signal, orthogonal to the first harmonic base signal, provided by the controller.

* * * * *